United States Patent
Koashi et al.

[11] Patent Number: 5,387,971
[45] Date of Patent: Feb. 7, 1995

[54] METHOD AND APPARATUS FOR MEASURING CONCENTRATION OF A SOLUTION USING PATHLENGTH COMPLEMENTALLY MODULATED CELLS

[75] Inventors: Katsue Koashi, Toyonaka; Atsuki Wada, Shiga, both of Japan

[73] Assignee: Kurashiki Boseki Kabushiki Kaisha, Kurashiki, Japan

[21] Appl. No.: 117,327

[22] Filed: Sep. 7, 1993

[30] Foreign Application Priority Data

Sep. 7, 1992 [JP] Japan ................... 4-238123

[51] Int. Cl.⁶ .................... G01N 1/10; G01J 1/00
[52] U.S. Cl. .................... 356/246; 356/436; 356/440; 250/344; 250/576
[58] Field of Search ............... 356/244, 246, 432, 433, 356/434, 435, 436, 437, 439, 440, 442, 73, 39, 410; 250/573, 576, 343, 344

[56] References Cited

U.S. PATENT DOCUMENTS

| | | |
|---|---|---|
| 2,761,067 | 8/1956 | Troy . |
| 3,679,899 | 7/1972 | Dimeff .................... 250/343 |
| 3,843,269 | 10/1974 | Hohberg .................... 356/246 |
| 3,899,252 | 8/1975 | Dimeff .................... 250/343 |
| 4,027,972 | 6/1977 | Davies .................... 250/343 |
| 4,937,448 | 6/1990 | Mantz et al. .................... 250/344 |
| 4,981,362 | 1/1991 | deJong et al. .................... 356/436 |

FOREIGN PATENT DOCUMENTS 0145877 1/1986 European Pat. Off. .
2014755 9/1971 Germany .

OTHER PUBLICATIONS

Frant et al., "Process Infrared Measurements," *Analytical Chemistry*, vol. 52, No. 12, Oct. 1980, pp. 1331A–1345A.

*Primary Examiner*—Hoa Q. Pham
*Attorney, Agent, or Firm*—Foley & Lardner

[57] ABSTRACT

Method and apparatus for measuring concentration of a solution use pathlength complementarily modulated cells comprising a sample cell and a reference cell arranged in parallel to each other and separated by a displacable separator window which is displaced parallelly in a direction of an optical axis of a measuring optical system thereby varying each of cell-length of sample and reference cells complementarily, detect transmitted intensities by the combined cells at different positions of the separator window while flowing a sample solution and a reference solution having a known concentration into the sample cell and reference cell, respectively, and calculate the concentration of the sample solution based on detected transmitted intensities, positions of the separator window at which transmitted intensities are detected and the known concentration of the reference solution.

13 Claims, 4 Drawing Sheets

METHOD AND APPARATUS FOR MEASURING CONCENTRATION OF A SOLUTION USING PATHLENGTH COMPLEMENTALLY MODULATED CELLS

BACKGROUND OF THE INVENTION

1. Field of the Invention

The present invention relates to method and apparatus for measuring concentration of a solution detecting a spectroscopic absorbance by the solution.

2. Description of the Related Art

In general, spectroscopic methods are widely used to determine the concentration of a chemical substance, and their fundamental principle is based on Lambert-Beer's law, which is expressed by the following formula (1).

$$A = abc = \log(I/T) \quad (1)$$

where

A: the absorbance of the sample at a characteristic absorption wavelength $\lambda$ of a specific component, T: the transmittance of the sample at the characteristic absorption wavelength $\lambda$ of the specific component, a: the absorptivity of the specific component at the characteristic absorption wavelength $\lambda$ of the specific component, b: cell length or pathlength, c: the concentration of the component in the sample.

T is expressed by the following formula (2).

$$T = I_t/I_0 \quad (2)$$

where $I_0$: the intensity of the incident light having the characteristic absorption wavelength $\lambda$, $I_t$: the intensity of the transmitted light having the characteristic wavelength $\lambda$.

If the sample is liquid, a cell is necessarily used. If the same cell is used for a sample having unknown concentration as for a standard sample having known concentration, the values of the absorptivity a and the cell length b need not be obtained. In fact, a and b are regarded as constant, and if k=ab, then formula (1) is simply expressed as the following formula (3).

$$A = kc \quad (3)$$

Once the value of the above constant k is determined by measuring the absorbance of a standard sample, the unknown concentration of the component in a sample is calculated and estimated by measuring the absorbance of the sample.

However, in order to implement the above method based on Lambert-Beer's law and to obtain data with precision, accuracy, reproducibility, and reliability, the following various problems have to be solved.

(1) The problem on the optical system.

A photometric signal varies with drifts caused by changes in the intensity of the light source and the fluctuation of the sensitivity of the photo detector. Unless these drifts are reduced and canceled, obtained data can not be trusted. Therefore, the light source and the photo detector have to be stabilized to reduce and prevent the drifts.

However, since the radiation from of a light source varies nonlinearly and deteriorates with time, its calibration is not easy. Even if some measures are taken under less than ideal condition, it is not guaranteed that there is no need of blank correction for a long time.

In particular, in process measurement of on-line and in-line systems, frequent blank correction is not only cumbersome and inconvenient, but also difficult.

Therefore, the stabilization of the light source and photo detector costs much but can not guarantee good results.

On the other hand, if a sample is liquid, it is necessary to perform measurement using a cell. In this case, apart from the true absorption of light by the sample, there are reflected components on the surfaces of cell windows due to the differences of the refractive indices among the cell window material, the sample, and the atmosphere, absorbed components by the cell windows themselves, a scattering component due to flaws of the cell, an absorbed component by stains, and a scattering component due to dust floating in the sample or suspensions in the sample. How to remove and cancel these components is an important factor in determining the precision and accuracy of the measurement.

(2) Problem on calibration curve

Between the concentration of a specific component in the sample and the sample's absorbance A there is a relationship expressed by the formula (3), which is a determining equation for concentration. However, actual measurement is not so simple, since device-dependent constants and experimental and measurement errors are involved. Therefore, a so-called calibration curve is drawn in the following way.

Many standard samples having known different concentrations are prepared considering the range of working concentrations. Then the constant k is determined by means of the least-square method to obtain the calibration curve. If the equation of the relationship between the absorbance and the concentration does not passes the origin, then an offset $k_0$ is added to the formula (3) to use the formula $A = kc + k_0$.

The calibration curve is sometimes not a straight line as in the above formulas, and a curve is used. Also, in case of a sample of a multi-component system, multivariate analysis is used.

The calibration curve is device-dependent, and compatibility and universality are not guaranteed. Also, an calibration curve once determined can not be used for a long time. The reliability of measurement is not maintained unless the calibration curve is regularly checked and corrected.

When a lamp of the light source or a cell is replaced, the judgment whether an established calibration curve is correct or not is not simple, but the recalibration is often required.

(3) Problem on spectrum analysis

In the spectrum of a sample of a liquid system, particularly an aqueous solution, a background signal of an aqueous solution is superimposed. The baseline shifts among the samples with drifts due to optical and electrical systems and often oblique and bent.

In order to correct the baseline shift, the so called two-wavelength method and the baseline method are used. In the two-wavelength method, a characteristic absorption peak wavelength is taken as a measuring wavelength, and a wavelength at the slope of a side of the peak or an isobestic wavelength is taken as a reference wavelength to obtain the ratio of intensities. In the baseline method, two wavelengths at the slope of both sides of the peak are taken as reference wavelengths, and a baseline is drawn at a slope of the reference wavelengths to measure the height of the peak from the baseline. In short, the difference between the two methods is how to set a reference level for the height of the peak. When the background signal of a solvent is superimposed, the baseline method is superior, but it costs more, since it uses three wavelengths.

Both the two-wavelength method and the baseline method are excellent techniques. However, these methods assume that the ratio of intensities of light source at a reference wavelength and at a measuring wavelength does not change. The profile of the spectrum of a light source is stable in a short time. But, in a long time, this ratio of intensities varies, and blank correction is required. If the light source is replaced or deteriorates, blank correction should be made again.

SUMMARY OF THE INVENTION

An object of the present invention is therefore to provide a method of measuring concentration that is excellent in precision, accuracy, reproducibility, stability, and reliability and does not require blank correction, and in which requirements for maintenance such as the cleaning of a cell are minimized.

Another object of the present invention is to provide an inexpensive apparatus for measuring concentration such that the user's various demands such as for simplification, modularization, and miniaturization can be satisfied, and the user can use the apparatus in the same manner as in using a thermometer, or a temperature controller and can install it in equipment and a system to easily obtain analog proportional control and optimal concentration range control.

In order to achieve the aforementioned first object, the method of measuring concentration of the present invention uses pathlength complementarily modulated cells comprising a sample cell and a reference cell separated by a separator window and serially arranged in the optical axial directions of the light path from a light source to a photo detector. A sample solution having unknown concentration is provided to the sample cell, and a reference sample having known concentration is provided to the reference cell. Desirably, the above separator window is periodically displaced in the optical axial direction of the optical system during a time in which drifts of the light source and the photo detector can be ignored, and the differences of absorbances, which are proportional to the differences of the concentrations between the sample cell and the reference cell, are detected from the output of the photo detector. Then the concentration of a component in the sample is calculated from the absorbance differences, the known concentration of the reference cell, and the amount of displacement of the separator window.

In order to achieve the second object, the apparatus for measuring concentration of the present invention comprises a light source, a photo detector that detects light from the light source, pathlength complementarily modulated cells comprising a sample cell and a reference cell separated by a separator window and serially arranged in the optical axial directions of the light path from the light source to the photo detector, a separator window driver that periodically displaces the separator window in the axial directions during a time in which drifts of the light source and the photo detector can be ignored, and an arithmetic means that calculates the differences of absorbances, which are proportional to the differences of the concentrations between the sample cell and the reference cell, from the output of the photo detector and calculates the concentration of a component in the sample from the absorbance differences, the known concentrations of the components in the reference cell, and the amount of displacement of the separator window.

Since the total pathlength of the sample cell and the reference cell is constant, if the length of the sample cell is increased by $\Delta b$, then the length of the reference cell is decreased by $\Delta b$. The separator window between the sample cell and the reference cell is displaced in the optical axial direction of the optical system. The arithmetic means obtains at least one difference of absorbances which are detected at different positions of the separator window. The arithmetic means then calculates the concentration of the solution in the sample cell from the absorbance difference, the known concentration of the reference cell, and the amount $\Delta b$ of displacement of the separator window.

The method of measuring concentration of the present invention calculates the concentration of a component in a sample based on an absorbance difference signal proportional to differences of concentrations between the sample cell and the reference cell owing to the displacement $\Delta b$ of the separator window. Since the combined cells do not change except the position of the separator window and each cell length, the difference of the total absorbance of the combined cells cancels light components reflected from the surface of the cell window, components scattered by flaws, components absorbed by the cells themselves, the absorption of the atmosphere, stray light, and the dark current of the detector. Since the displacement $\Delta b$ of the separator window is performed in a short time in which drifts of the light source and the photo detector can be ignored, the effects of drifts of the light source and the photo detector are also canceled. Therefore, the precision, accuracy, sensitivity, and reproducibility are improved and blank correction becomes unnecessary.

The instrument for measuring concentration of the present invention has pathlength complementarily modulated cells in which the separator window is periodically displaced by a constant length and determines the unknown concentration of a component of a sample from the differences of absorbances proportional to differences concentrations between the sample cell and the reference cell, the known concentration of the component in the reference sample, and the amount of displacement of the separator window. Since the combined cells do not change except the position of the separator window and each cell length, the differences of the total absorbances of the combined cells cancel reflected components on the surfaces of the cell windows, a scattering component due to flaws, absorbed components by the cell windows themselves, the absorption of the atmosphere, stray light, and the dark current of the detector. Since the displacement of the separator window is performed in a short time in which drifts of the light source and the photo detector can be ignored, the effects of drifts of the light source and the photo detector are also canceled, and simplification, modularization, and miniaturization are made easy. Therefore, the user can use the instrument in the same attitude as in using a thermometer, or a temperature controller and can install it in equipment and a system to easily obtain analog proportional control and optimal concentration range control.

BRIEF DESCRIPTION OF THE DRAWINGS

These and other objects and features of the present invention will become clear from the following description taken in conjunction with the preferred embodiments thereof with reference to the accompanying drawings throughout which like parts are designated by like reference numerals, and in which.

DETAILED DESCRIPTION OF THE PREFERRED EMBODIMENTS

The preferred embodiments according to the present invention will be described below with reference to the attached drawings.

Figure 1:
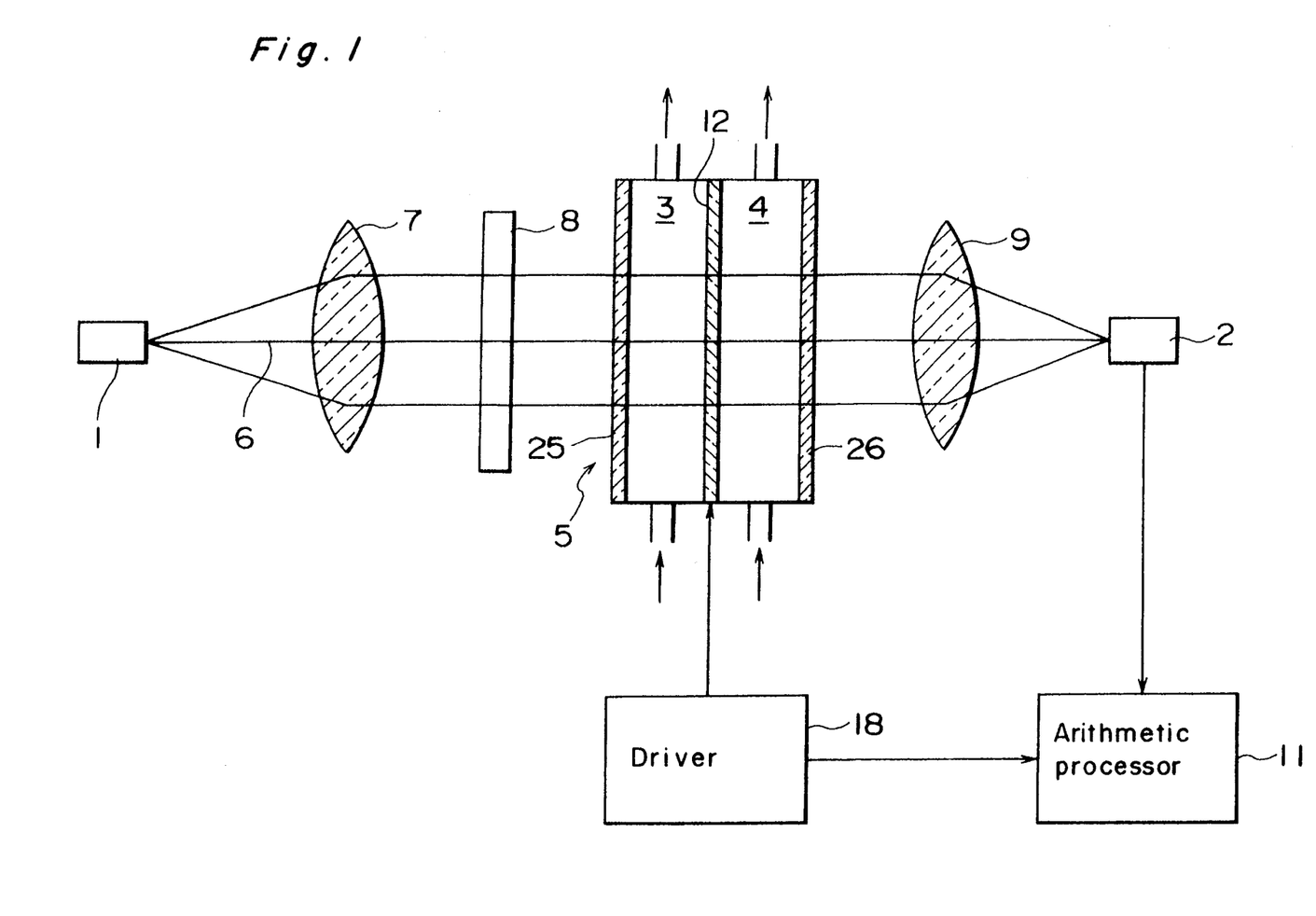
FIG. 1 is shows a block diagram of an embodiment of an apparatus for measuring concentration in accordance with the present invention.

As shown in FIG. 1, the apparatus has an optical system arranged along a light path from a light source 1 to a photo detector 2. On the optical axis 6 of the optical system, there are arranged a collimator lens 7 for collimating light emitted from the light source 1, a monochrometer 8 for passing only a light component having a wavelength which is equal to a characteristic absorption wavelength of a solute contained in a solution to be measured, pathlength complimentarily modulated cells 5 comprising a sample cell 3 and a reference cell 4 arranged in parallel to each other and separated by a separator window 12 and a collecting lens 9 for collecting the light transmitted through the combined cells 5. The output of photo detector 2 is input to an arithmetic processor 11.

Here, a white light source such as a incandescent lamp or a light emitting element such as a light emitting diode can be used as light source 1. An optical filter or grating can be used as monochrometer 8.

Figure 2:
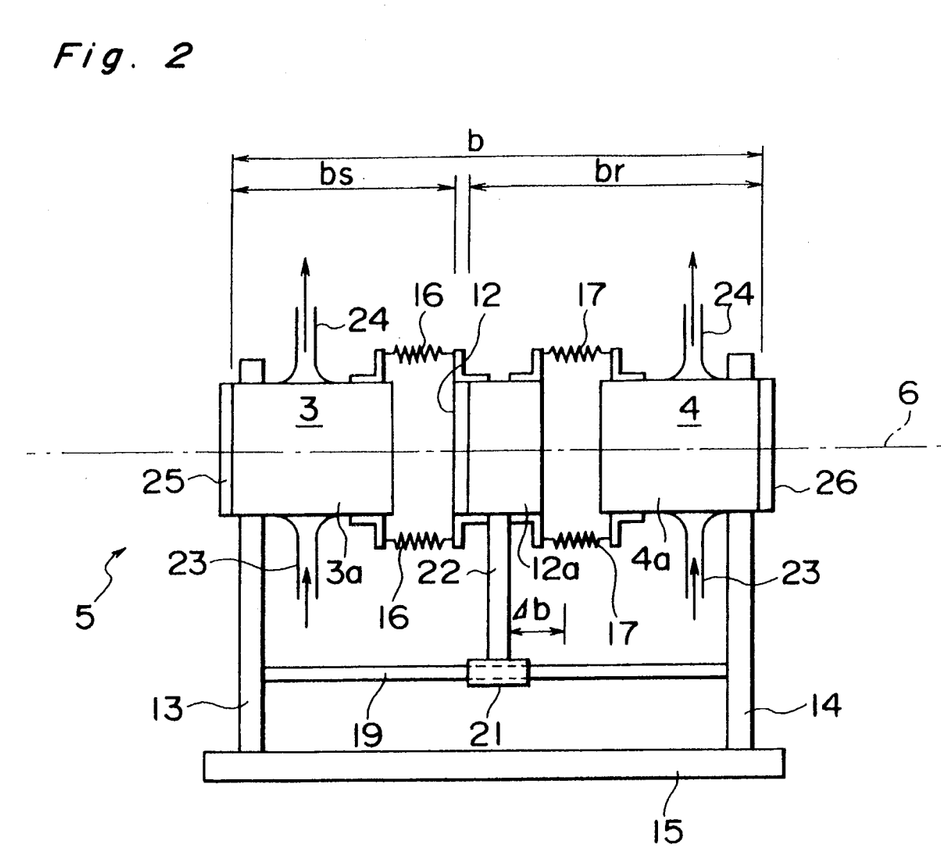
FIG. 2 shows a configuration of pathlength complementarily modulated cells used in the apparatus of FIG. 1.

Pathlength complementarily modulated cells 5 are configured as shown in FIG. 2. Sample cell 3 and reference cell 4 of pathlength complementarily modulated cells 5 are separated from each other by a separator window 12.

Sample cell 3 has a cell cylinder 3a and a cell window 25, and reference cell 4 has a cell cylinder 4a and a cell window 26. The cell cylinder 3a and cell cylinder 4a have their coincident optical axis 6 and are fastened to a stand 15 by columns 13 and 14 at an interval that allows a support cylinder 12a of separator window 12 to move in the directions of optical axis 6. Cell cylinder 3a and support cylinder 12a are connected by bellows 16, and cell cylinder 4a and support cylinder 12a are connected by bellows 17.

A worm 19 is supported by columns 13 and 14 and rotated by a driver 18 of FIG. 1. Support cylinder 12a of separator window 12 is attached to a thread part, which is spirally attached to worm 19, by a connector 22. Support cylinder 12a of separator window 12 has the same optical axis as optical axis 6 of cell cylinders 4a and 3a.

Worm 19 is rotated by driver 18, so that thread part 21 spirally attached to it is displaced in the optical axial directions of worm 19, and separator window 12 repeats a parallel and reciprocating movement between cell cylinder 4a of reference cell 4 and cell cylinder 3a of sample cell 3.

The amount $\Delta b$ of displacement of separator window 12 is detected, for example, by driver 18 from a limiter signal, which is output by limiters (not shown) installed on worm 19, when thread part 21 makes contact with one of the limiters, and the amount of rotation of worm 19. The amount $\Delta b$ of displacement of separator window 12 can also be detected by installing a potentiometer (not shown) on thread part 21 and by reading the output of the potentiometer.

As shown by arrows, a sample solution and a reference solution are respectively provided to cell cylinder 3a of sample cell and cell cylinder 4a of reference cell through entrance ports 23 located below by appropriate supplying means (not shown) and drained through exit ports 24 located above. In this case, pathlength complementarily modulated cells 5 become flow cells.

In the apparatus for measuring concentration described above, the total cell length b of pathlength complementarily modulated is constant. Therefore, if separator window 12 moves in a direction of optical axis 6, and the cell length $b_s$ of sample cell 3 increases by $\Delta b$, then the cell length $b_r$ of reference cell 4 decreases by $\Delta b$ as shown in the following formula (4). Conversely, if the cell length $b_s$ of sample cell 3 decreases by $\Delta b$, then the cell length $b_r$ of reference cell 4 increases by $\Delta b$.

$$b = b_s + b_r = \text{Constant} = (b_s + \Delta b) + (b_r - \Delta b) \tag{4}$$

The change $\pm \Delta b$ of the cell length $b_s$ of sample cell 3 and the cell length $b_r$ of reference cell 4 is given to arithmetic processor 11 as a detected signal by driver 18 shown in FIG. 1. Arithmetic processor 11 calculates the concentration of sample cell 3 in the following way.

(1) Two-component sample

Let the concentrations of component 1 and component 2 of a two-component sample be respectively $c_1$ and $c_2$, and let the absorptivities of component 1 and component 2 be respectively $a_1$ and $a_2$. Further, to distinguish sample cell 3 and reference cell 4, let the concentrations of component 1 and component 2 in sample cell 3 be respectively $c_{1s}$ and $c_{2s}$, and let the concentrations of component 1 and component 2 in reference cell 4 be respectively $c_{1r}$ and $c_{2r}$. Here these concentrations are normalized values, that is, $$c_{1s} + c_{2s} = 1 \tag{5}$$

$$c_{1r} + c_{2r} = 1 \tag{6}$$

Consider the absorbance $A_s$ of sample cell 3, the absorbance $A_r$ of reference cell 4, and the total absorbance A. Assume that there is no chemical interaction between the components, or take a range of wavelengths where chemical interaction can be ignored. From Lambert-Beer's law it follows that $$A_s = a_1 b_s c_{1s} + a_2 b_s c_{2s} \tag{7}$$

$$A_r = a_1 b_r c_{1r} + a_2 b_r c_{2r} \tag{8}$$

The total absorbance A of pathlength complementarily modulated cells 5 is the simple sum of the absorbance $A_s$ of sample cell 3 and the absorbance $A_r$ of reference cell 4. Therefore $$A = A_s + A_r \qquad (9)$$
$$= a_1(b_s c_{1s} + b_r c_{1r}) + a_2(b_s c_{2s} + b_r c_{2r})$$

On the other hand, the absorbance A is expressed in terms of the transmittance T of pathlength complementarily modulated cells 5 and the observed intensities $I_0$ and $I_t$ of incident light and transmitted light by $$A = \log(1/T) = \log(I_0/I_t) \qquad (10)$$

If, in these conditions, the cell length $b_s$ of sample cell 3 of pathlength complementarily modulated cells 5 increased by $\Delta b$, and the cell length $b_r$ of reference cell 4 decreases by $\Delta b$, then the absorbance $A'_s$ of sample cell 3 and the absorbance $A'_r$ of reference cell 4 are expressed by the following formulas (11) and (12), respectively.

$$A'_s = a_1(b_s + \Delta b)c_{1s} + a_2(b_s + \Delta b)c_{2s} \qquad (11)$$

$$A'_r = a_1(b_r + \Delta b)c_{1r} + a_2(r_s + \Delta b)c_{2r} \qquad (12)$$

The total absorbance $A'$ of pathlength complementarily modulated cells 5 is the simple sum of the absorbance $A'_s$ of sample cell 3 and the absorbance $A'_r$ of reference cell 4. Therefore $$\begin{aligned}A' &= A'_s + A'_r \qquad (13)\\ &= a_1(b_s c_{1s} + b_r c_{1r}) + a_2(b_s c_{2s} + b_r c_{2r}) +\\ &\quad a_1 \Delta b(c_{1s} - c_{1r}) + a_2 \Delta b(c_{2s} - c_{2r})\\ &= A + a_1 \Delta b(c_{1s} - c_{1r}) + a_2 \Delta b(c_{2s} - c_{2r})\end{aligned}$$

On the other hand, the total absorbance $A'$ is expressed in terms of the transmittance $T'$ of pathlength complementarily modulated cells 5 and the observed intensities $I_0'$ and $I_t'$ of incident light and transmitted light by $$A' = \log(1/T') = \log(I_0'/I_t') \qquad (14)$$

From formulas (13) the difference $\Delta A = A' - A$ of the total absorbances is obtained as $$\begin{aligned}\Delta A &= A' - A \qquad (15)\\ &= a_1 \Delta b(c_{1s} - c_{1r}) + a_2 \Delta b(c_{2s} - c_{2r})\end{aligned}$$

It should be noted that the difference $\Delta A$ of absorbances here is not a difference between absorbances at a measuring wavelength $\lambda_s$ and a reference wavelength $\lambda_r$ in the double-wavelength method, but a difference between absorbances at the same wavelength.

On the other hand, from (10) and (14) the difference $\Delta A$ of absorbances are obtained in terms of the transmittances and the observed intensities of light as $$\begin{aligned}\Delta A &= A' - A \qquad (16)\\ &= \log(1/T') - \log(1/T)\\ &= \log(I_0'/I_t') - \log(I_0/I_t)\end{aligned}$$

The value of the difference $\Delta A$ of absorbances is obtained by the output of photo detector 2 and formula (16). Therefore, the unknown values of concentrations $c_{1s}$ and $c_{2s}$ of components 1 and 2 in sample cell 3 is obtained from formula (5) and (15) using the known values of concentrations $c_{1r}$ and $c_{2r}$ of components 1 and 2 in reference sample 4 and the known amount $\Delta b$ of displacement of separator window 12.

Although not expressed in the above formulas, the subtractions in calculating the difference $\Delta A$ of total absorbances cancel reflected components on the surfaces of cell windows 25 and 26, a scattering component due to flaws, absorbed components by cell windows 25 and 26 themselves, and absorbed components by stains and the atmosphere as well as stray light and the dark current of the detector. Therefore, invalid and detrimental components are canceled, and a value near the absolute difference of absorbances can be measured, that is, a device-independent calibration curve can be obtained. Since the above subtractions cancel reflected and absorbed components inherent to cells, compatibility of cells is satisfied. Further, since stains of cells are canceled, the frequency of necessary cleaning can also be reduced.

(2) Multi-component sample

Formula (15) described above for a two-component sample is generalized to the following formula (17) for a multi-component sample.

$$\begin{aligned}\Delta A &= A' - A \qquad (17)\\ &= a_1 \Delta b(c_{1s} - c_{1r}) + a_2 \Delta b(c_{2s} - c_{2r}) +\\ &\quad a_3 \Delta b(c_{3s} - c_{3r}) + a_4 \Delta b(c_{4s} - c_{4r}) + \ldots\end{aligned}$$

Now we determine that concentration of component 1 in a two-component sample, we select a wavelength among characteristic absorption wavelengths of component 1 such that its absorptivity is large and not effected by component 2. If $$a_1 \gg a_2, \ a_2 \sim 0 \qquad (18)$$

then the contribution of the first term of formula (15) is dominant in the absorbance difference $\Delta A$.

Conversely, we determine that concentration of component 2, we select a wavelength among characteristic absorption wavelengths of component 2 such that its absorptivity is large and not effected by component 1. In fact, if $$a_2 \gg a_1, \ a_1 \sim 0 \qquad (19)$$

then the contribution of the second term of formula (15) is dominant in the absorbance difference $\Delta A$.

On the other hand, if formulas (5) and (6) expressing relationships between concentrations are applied to formulas (15), then the following formulas (20) and (21) are obtained.

$$\begin{aligned}\Delta A &= A' - A \qquad (20)\\ &= (a_1 - a_2)\Delta b(c_{1s} - c_{1r})\end{aligned}$$

$$\begin{aligned}\Delta A &= A' - A \qquad (21)\\ &= (a_2 - a_1)\Delta b(c_{2s} - c_{2r})\end{aligned}$$

In the above formulas (20) and (21), since the absorptivities $a_1$ and $a_2$ are constant, $a_1 - a_2$ is constant. Therefore, the absorbance difference $\Delta A$ is proportional to the difference of absorbances of component 1 in sample cell 3 and reference cell 4:

$$c_{1s} - c_{1r} \qquad (22)$$

Similarly, the absorbance difference $\Delta A$ is proportional to the difference of absorbances of component 2 in sample cell 3 and reference cell 4:

$$c_{2s} - c_{2r} \qquad (23)$$

These properties are due to the complementary relationships between concentrations in a two-sample system expressed by (5) and (6).

By applying known concentrations $c_{1r}$ and $C_{2r}$ in the reference cell to formulas (20) and (21), concentrations $c_{1s}$ and $c_{2s}$ in the sample cell are obtained.

(3) Single-component reference cell

This case represents that the reference solution contains only a solvent, such as water in a case of an aqueous solution. In this case formula (6) becomes $$c_{1r} = 1, \ c_{2r} = 0 \qquad (24)$$

Therefore, formulas (20) and (21) become the following (25) and (26).

$$\begin{aligned}\Delta A &= A' - A \\ &= (a_1 - a_2)\Delta b (c_{1s} - 1)\end{aligned} \qquad (25)$$

$$\begin{aligned}\Delta A &= A' - A \\ &= (a_2 - a_1)\Delta b c_{2s}\end{aligned} \qquad (26)$$

Therefore, the absorbance difference $\Delta A$ is simply proportional to the concentration $C_{2s}$ of component 2 in sample cell 3. From the above formulas (25) and (26) and the absorbance difference $\Delta A$, concentrations $c_{1s}$ and $c_{2s}$ can be obtained.

If we use a sample cell having a known concentration $c_{2s}$ of component 2 and a wavelength among characteristic absorption wavelengths of component 2 such that formula (19) is satisfied, that is, its absorptivity is large and not effected by component 1, then from the absorbance difference at that wavelength and formula (26) we can obtain a device-independent absorptivity $a_2$ of component 2. This value of absorptivity is useful in concentration analysis for multi-component systems.

Good measurement is often obtained even if a single wavelength is used. If a light emitting diode for an optimal wavelength is available, a filter is not required, and the optical system can be made compact.

If a single component different from a component in sample cell 3 is used for reference cell, and if its absorbance characteristics are known, then the actual amount of displacement of cell lengths or its calibration can be obtained.

(4) Multi-component sample cell and single component reference cell

If sample cell 3 is a multi-component system, and reference cell 4 is a single component system, then formulas (5) and (17) are respectively expressed as the following (27) and (28).

$$c_{1s} + \Sigma c_{is} = 1 \qquad (27)$$

$$\begin{aligned}\Delta A &= A' - A \\ &= a_1 \Delta b (c_{1s} - 1) + \Sigma a_{is} \Delta b c_{is}\end{aligned} \qquad (28)$$

In general a solvent occupies most part of sample cell 3 and produces a background spectrum. In particular, in case of an aqueous solution, the background of water is great and easily affected by drifts of a spectrometer. The accuracy of detection depends on how much to cancel these drifts.

$c_{1s} - 1$ in the first term of formula (28) is the difference between the concentrations of the solvents in sample cell 3 and reference cell 4. It is not completely canceled, but, in most cases, almost zero. The second term $\Sigma a_i \Delta b c_{is}$ has significant information for component analysis. In general, a regression method is applied to build a calibration curve for obtaining an individual concentration.

As described above, an individual absorptivity can be obtained by experiment. Therefore, in many cases, a simple analysis suffices by selecting appropriate wavelengths, so that cumbersome regression analysis is not necessary.

In the above description, the reference cell is a solvent consisting of a single component. However, if a reference sample is made by selecting an appropriate combination of components in the sample cell, a difference spectrum between sample and reference by pathlength complementarily modulated cells 5 are obtained, as is clear from formula (17).

(5) On relationship formula (16) between the absorbance difference and observed intensities Drifts of light source 1 and photo detector 2 are long term fluctuations or instability, so that if the displacement $\Delta b$ is made in such a very short time, effects of drifts on the observed intensities $I_0$ and $I_0'$ of the incident light can be ignored. That is, $$I_0 = I_{0'} \qquad (29)$$

Therefore, the absorbance difference $\Delta A$ is expressed by the following formula (30).

$$\begin{aligned}\Delta A &= A' - A \\ &= \log (I_0'/I_t') - \log (I_0/I_t) \\ &= \log I_t - \log I_t' \\ &= \log (I_t/I_t')\end{aligned} \qquad (30)$$

To estimate a time period for which the above drifts can be ignored, let drifts of observed signals concerning light source 1 and photo detector 2 and others be 1 percent per 1 hour in terms of observed signal intensities. Then the equivalent drifts per 1 second become less than $10^{-5}$. To obtain the signal to noise ratio (S/N) of $10^5$, the displacement $\Delta b$ may be made in the order of seconds. When the displacement is repeated, i.e. modulated, the modulation may be made at less than a few hertz. This condition changes with required precision, but can be realized.

Under the short term conditions in which effects of drifts can be ignored, if observed signal intensities are cumulatively averaged, the random noise decreases in proportion to the square root of the cumulative frequency. If drifts are great, then the random noise does not decreases even if the signal intensities are cumulatively averaged.

On the other hand, the absorbance difference in the ordinary two-wavelength method is the difference $\Delta A_t$ between the absorbances $A(\lambda_s)$ and $A(\lambda_r)$ at the measuring wavelength $\lambda_s$ and the reference wavelength $\lambda_r$ and expressed by the following formula (31).

$$\Delta A_t = A(\lambda_s) - A(\lambda_r) \qquad (31)$$
$$= \log \{I_0(\lambda_s)/I_t(\lambda_s)\} - \log \{I_0(\lambda_r)/I_t(\lambda_r)\}$$

where $I_0(\lambda_s)$: incident intensity at wavelength $\lambda_s$
$I_t(\lambda_s)$: transmitted intensity at wavelength $\lambda_s$
$I_0(\lambda_r)$: incident intensity at wavelength $\lambda_r$
$I_t(\lambda_r)$: transmitted intensity at wavelength $\lambda_r$ If the ratio of the incident intensities at the measuring wavelength and at the reference wavelength is a constant k, that is, $$I_0(\lambda_s) = k I_0(\lambda_r) \qquad (32)$$

then $$\Delta A_t = \log k = \log \{I_t(\lambda_r)/I_t(\lambda_s)\} \qquad (33)$$

The profile of the emission spectrum of a light source is stable in a short time. However, in a long time, the spectrum of the light source changes and the ratio k of the incident intensities changes. Therefore, the ordinary two-wavelength method requires blank correction to compensate the change. If the light source is replaced or degraded, calibration depending on the change of the intensity ratio k becomes necessary.

The method of measuring concentration in the embodiment described above can obtain a true absorbance difference by canceling the background signal, so that it realizes measurement having sufficient precision at a single characteristic absorption wavelength without using the two-wavelength method or the baseline method. Moreover, the electric and optical compositions are simple. If an individual component is to be separated from a complex spectrum of a multi-component system to measure concentration, several different wavelengths may be used.

(6) Experimental results

Figure 4:
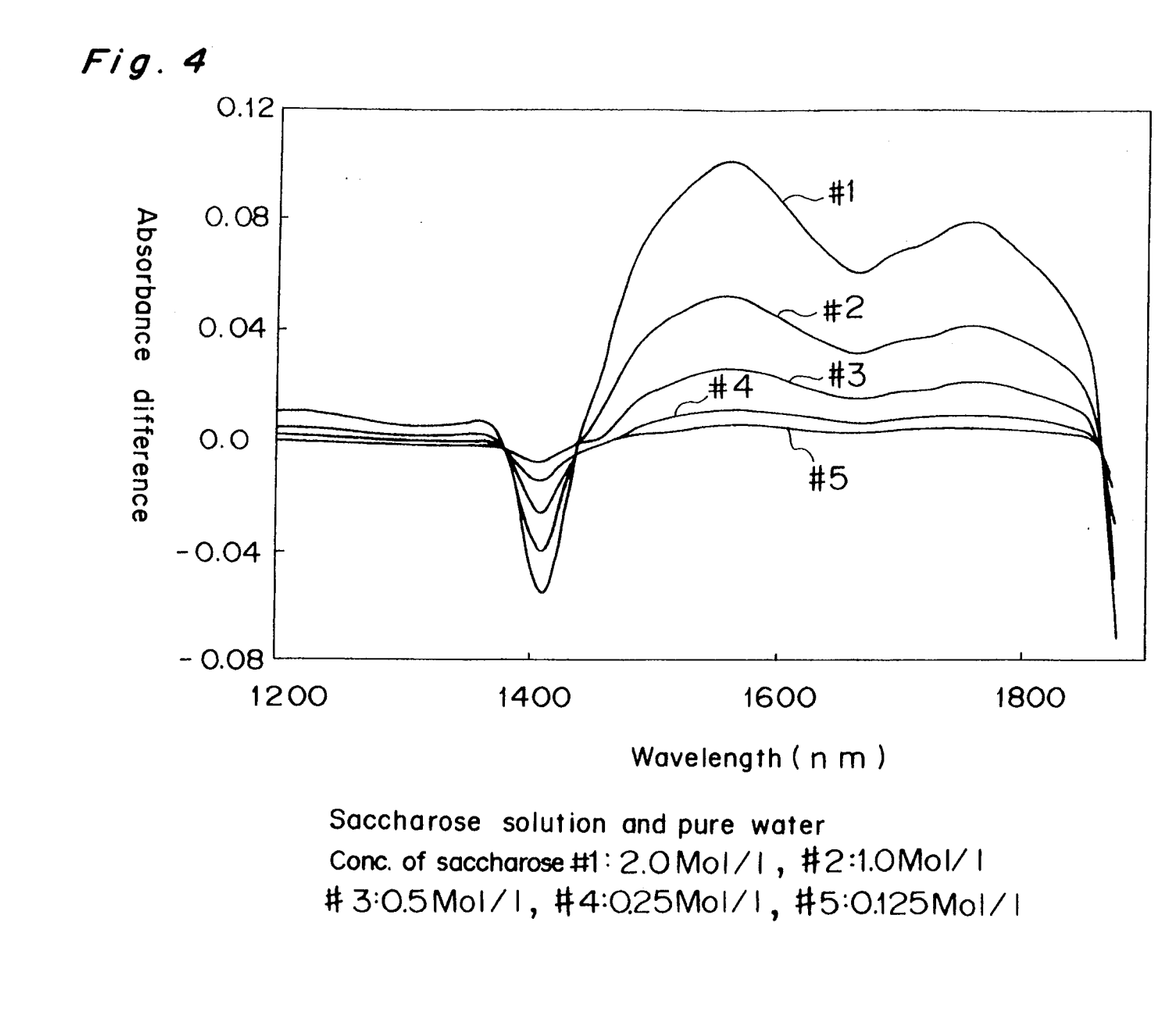
FIG. 4 shows a graph of a measurement result obtained by measuring the absorbance differences of aqueous saccharose solutions having five different concentrations using the pathlength complementarily modulated cells of FIG. 2.

Pathlength-complementarily modulated cells 5 of FIG. 2 were used. Reference cell 4 was pure water. Sample cell 3 was varied as aqueous saccharose solutions having concentrations of 2.0 mol/l, 1.0 mol/l, 0.5 mol/l, 0.25 mol/l, and 0.125 mol/l. The displacement $\Delta b$ was approximately 1 mm. The measured results of the absorbance differences of each solution are shown in FIG. 4. As observed from FIG. 4, the absorbance differences change in proportion to the concentration of saccharose in the range of wavelengths from 1500 nm to 1800 nm.

In the embodiment described so far, simple measurement may be conducted by manually displacing separator window 12 between the limiters using a lever handle (not shown in FIG. 2) attached to support cylinder 12a.

Figure 3:
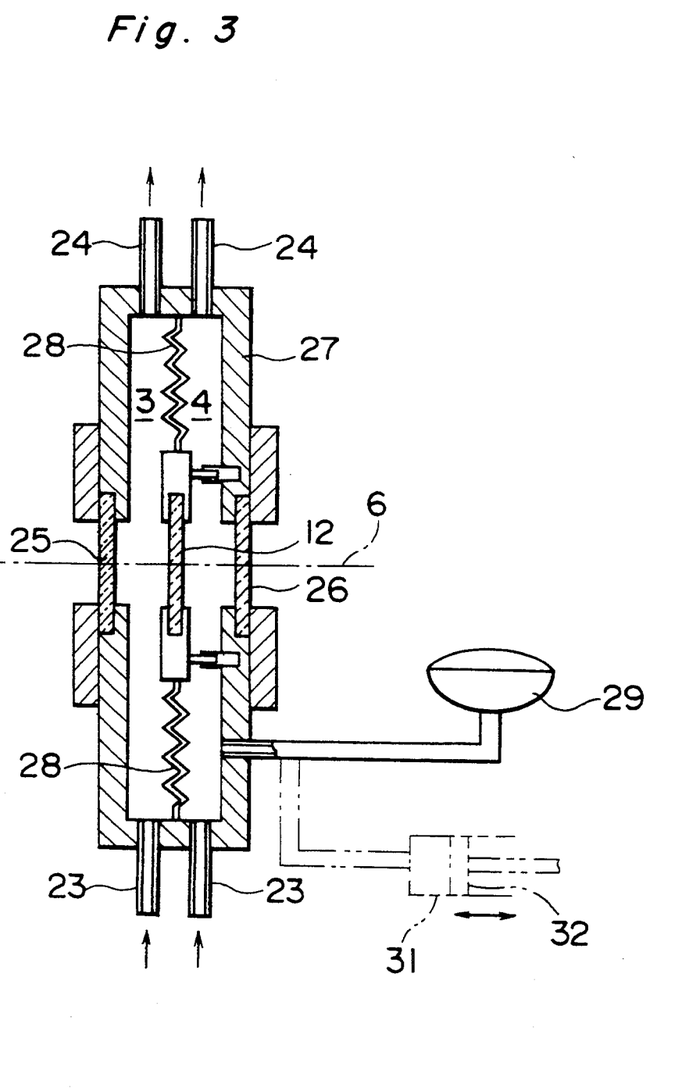
FIG. 3 shows another configuration of pathlength complementarily modulated cells.

Further, in place of pathlength-complementarily modulated cells 5 shown in FIG. 2, a casing 27 having optical windows 25 and 26 at opposite walls as shown in FIG. 3 can be used. Casing 27 is separated into a sample cell 3 and a reference cell 4 by a separator window 12, which is supported by a displacement film 28 made of rubber or metal. Separator window can be displaced by a diaphragm device 29 or a piston pump 31 communicating with reference cell 4. 32 is a piston reciprocating in the directions of the bidirectional arrow. Other numerals In FIG. 3 represent the same corresponding components as in FIG. 2.

(7) Application to concentration controller

An embodiment of an application of the present invention to a concentration controller is described in the following.

Concerning the formulas (20) and (21) for two-component systems, conditions on concentrations of sample cell 3 and reference cell 4 are classified into the following three cases based on their order relations. A characteristic absorption wavelength is selected so that $a_1 - a_2 > 0$ ($a_1 >> a_2$ and $a_2 \sim 0$, if possible).

(i) The concentration $c_{1s}$ of sample cell 3 is greater than the concentration $c_{1r}$ of reference sample 4 ($c_{1s} > c_{1r}$). The absorbance difference $\Delta A$ becomes positive ($\Delta A > 0$), and its magnitude is proportional to the concentration difference $c_{1s} - c_{1r}$.

(ii) The concentration $c_{1s}$ of sample cell 3 is less than the concentration $c_{1r}$ of reference cell 4 ($c_{1s} < c_{1r}$). The absorbance difference $\Delta A$ becomes negative ($\Delta A < 0$), and its magnitude is proportional to the concentration difference.

(iii) The concentration $c_{1s}$ of sample cell 3 is equal to the concentration $c_{1r}$ of reference cell 4 ($c_{1s} = c_{1r}$). The absorbance difference $\Delta A$ becomes zero ($\Delta A = 0$), and the absorbance difference $\Delta A$ does not change even if $\Delta b$ changes.

The absorbance difference $\Delta A$ is a signal proportional to the concentration difference $c_{1s} - c_{1r}$, so that the signal $\Delta A$ is suitable for on-line concentration control. If $c_{1r}$ is chosen to be a considered standard concentration of a considered component, then the detection and control of the difference between the concentration of the sample cell and the standard concentration are easily achieved. The building of calibration curves, which requires manpower and experiences, is not necessary.

If the displacement $\Delta b$ is continuously and smoothly varied at constant speed, then the concentration difference between sample cell 3 and reference cell 4 is proportional to the temporal rate of change of the absorbance difference. In this case, an advantage is that a continuous signal is obtained instead of an intermittent signal. If a log amplifier is used for processing of formula (30), A/D conversion is not necessary, so that high-degree control can be achieved by a simple controller.

As another application, if two sets of pathlength complementarily modulated cells are used, so that the concentration of the reference cell of one set is set at an upper bound of acceptable concentration, and the concentration of the reference cell of the other set is set to an lower bound of acceptable concentration, then admissible concentration control is easily realized.

The instrument and method of the present invention are most fit for the process of concentration, dilution, and extraction. They are also convenient for examining changes difficult to measure and quantify, such as degradation or denaturation, in comparing an old product with a standard or a new product. For example, they are applied to evaluate degradation of engine oil and machine oil.

(8) Application to turbidimeter

An embodiment of application of the present invention to a turbidimeter is described in the following. The present invention is not only effective to measure a turbid sample, but also applicable to a turbidimeter.

Turbidity is a decreased amount of light passing through a solvent such as water due to scattering by floating particles. A turbidimeter normalizes transmitted light by incident light. However, the amount of incident light is device-dependent and hard to measure with accuracy and precision. Also, the expression of scattering characteristics is hard owing to the lack of standards.

When the present invention is applied to a turbidimeter, the concentration of particles $c_{2s}$ is obtained from formulas (24) and (25). In these formulas, the coefficient $a_2-a_1$ is regarded as a scattering coefficient in a solvent or a coefficient equivalent to a scattering cross section rather than a difference of absorptivities.

The subtractions in calculating the difference $\Delta A$ of total absorbances cancel invalid and detrimental components such as reflected components on the surfaces of cell windows, a scattering component due to flaws, an absorbed component by cell material itself, and absorbed components by stains and so forth. Therefore, a value near the absolute difference of absorbances, i.e. a device-independent value, can be measured. Since the above subtractions cancel reflected and absorbed components inherent to cells, compatibility of cells is also satisfied. Further, since stains of cells, which often cause trouble for a turbidimeter, are canceled, the frequency of necessary cleaning can also be reduced.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. A concentration measuring method for measuring concentration of a solution by detecting a spectroscopic absorbance of light by said solution comprising steps of
   arranging pathlength complementarily modulated cells serially on a light path from a light source to a photo detector which consist of a sample cell and a reference cell separated by a displacable separator window,
   providing said sample cell with a sample solution having an unknown concentration while providing said reference cell with a reference solution having a known concentration,
   parallelly-displacing said separator window on said light path,
   detecting the absorbance by said pathlength complementarily modulated cells at least two different positions of said separator window from the output of said photo detector thereby obtaining at least one absorbance difference, and calculating the concentration of said sample solution from said at least one absorbance difference, said known concentration of said reference solution and respective positions of said separator window at which the absorbance is measured.

2. The concentration measuring method according to claim 1 wherein said separator window is periodically displaced within a predetermined distance and measurement of the absorbance is performed at a predetermined time interval within one cycle of displacement.

3. The concentration measuring method according to claim 2 wherein the measurement of the absorbance is performed within a time in which drifts of said light source and photo detector can be ignored.

4. The concentration measuring method according to claim 1 wherein said separator window is driven at a predetermined velocity.

5. The concentration measuring method according to claim 1 wherein said solution is two-component system consisting of a solvent and a solute.

6. The concentration measuring method according to claim 1 wherein said solution is multi-component system consisting of a solvent and two or more solutes.

7. The concentration measuring method according to claim 6 wherein the measurement is performed using two or more lights each including a characteristic absorption wavelength of each of the multi-components at which absorption by other components is negligible.

8. An apparatus for measuring the concentration of a solution by detecting a spectroscopic absorbance of light by said solution comprising,
   a light source for irradiating light having at least one characteristic absorption wavelength of a component contained in said solution,
   a photo detector for outputting electric signal corresponding to a spectrum of the light received thereby,
   pathlength complementarily modulated cells comprising a sample cell into which a sample solution having unknown concentration is supplied and a reference cell into which a reference solution having known concentration is supplied, said cells separated by a displacable separator window and serially arranged serially on a light path from said light source to said photo detector,
   a driving means for parallelly displacing said separator window on said light path within a predetermined range,
   an arithmetic means for calculating the absorbance at least two positions of said separator window form the output of said photo detector thereby obtaining at least one absorbance difference dependent on the position of said separator and calculating the concentration of said solution from said at least one absorbance difference, said known concentration of said reference solution and respective positions of said separator window at which the absorbance is measured.

9. The apparatus for concentration measurement according to claim 8 further comprising a monochrometer means for passing only light having said characteristic absorption wavelength.

10. The apparatus for concentration measurement according to claim 9 further comprising a collimator lens for collimating light emitted from said light source and a collecting lens for collecting the light collimated by said collimator lens.

11. The apparatus for concentration measurement according to claim 8 wherein said driving means is means for displacing said separator window periodically within a predetermined range.

12. The apparatus for concentration measurement according to claim 8 wherein the period of displacement of said separator window is reasonable smaller than the unstable and transition period of said light source and photo detector.

13. A path length complimentarily-modulated cell assembly comprising a sample cell and a reference cell arranged in series and separated by a displacable separator window, said displacable separator window being displacable in a direction such that respective path lengths of the sample cell and the reference cell are varied complementarily when the separator window is displaced, while the total path length of the sample cell and reference cell remains constant.

* * * * *